US011964266B2

(12) United States Patent
Lewis et al.

(10) Patent No.: US 11,964,266 B2
(45) Date of Patent: Apr. 23, 2024

(54) PROCESS FOR REMOVING COBALT, LEAD, CADMIUM AND CHROMIUM IONS FROM BODILY FLUIDS USING METALLATE ION EXCHANGE COMPOSITIONS

(71) Applicant: UOP LLC, Des Plaines, IL (US)

(72) Inventors: Gregory John Lewis, Santa Cruz, CA (US); Paulina Jakubczak, Elk Grove Village, IL (US); Julio C. Marte, Carol Stream, IL (US); William Christopher Sheets, Glenview, IL (US)

(73) Assignee: UOP LLC, Des Plaines, IL (US)

( * ) Notice: Subject to any disclaimer, the term of this patent is extended or adjusted under 35 U.S.C. 154(b) by 1318 days.

(21) Appl. No.: 16/506,377

(22) Filed: Jul. 9, 2019

(65) Prior Publication Data

US 2021/0008266 A1  Jan. 14, 2021

(51) Int. Cl.
| | | |
|---|---|---|
| *B01J 39/02* | (2006.01) | |
| *A61M 1/16* | (2006.01) | |
| *A61M 1/28* | (2006.01) | |
| *A61M 1/34* | (2006.01) | |
| *A61M 1/36* | (2006.01) | |
| *B01D 15/36* | (2006.01) | |
| *B01D 69/02* | (2006.01) | |
| *B01D 69/08* | (2006.01) | |
| *B01J 39/09* | (2017.01) | |
| *B01J 39/10* | (2006.01) | |
| *B01J 39/26* | (2006.01) | |
| *B01J 47/018* | (2017.01) | |
| *B01J 47/02* | (2017.01) | |
| *B01J 47/127* | (2017.01) | |
| *A61K 9/50* | (2006.01) | |

(52) U.S. Cl.
CPC ............ *B01J 39/02* (2013.01); *A61M 1/1696* (2013.01); *A61M 1/287* (2013.01); *A61M 1/3486* (2014.02); *A61M 1/3679* (2013.01); *A61M 1/3687* (2013.01); *B01D 15/362* (2013.01); *B01D 69/02* (2013.01); *B01D 69/08* (2013.01); *B01J 39/09* (2017.01); *B01J 39/10* (2013.01); *B01J 39/26* (2013.01); *B01J 47/018* (2017.01); *B01J 47/02* (2013.01); *B01J 47/127* (2017.01); *A61K 9/5042* (2013.01); *B01D 2311/2626* (2013.01); *B01D 2313/40* (2013.01); *B01D 2325/12* (2013.01); *B01D 2325/42* (2013.01)

(58) Field of Classification Search
CPC .... A61M 1/1678; A61M 1/1696; A61M 1/28; A61M 1/287; A61M 1/3486; A61M 1/3679; A61M 1/3687; B01D 15/362; B01D 61/28; B01D 69/02; B01D 69/08; B01D 2311/2626; B01D 2313/40; B01D 2325/12; B01D 2325/42; B01J 39/02;

B01J 39/09; B01J 39/26; B01J 47/016; B01J 47/018; B01J 47/02; B01J 47/127; B01J 39/10; A61K 9/5042

See application file for complete search history.

(56) References Cited

U.S. PATENT DOCUMENTS

| | | | |
|---|---|---|---|
| 4,261,828 | A | 4/1981 | Brunner et al. |
| 4,581,141 | A | 4/1986 | Ash |
| 4,612,122 | A | 9/1986 | Ambrus et al. |
| 5,053,139 | A | 10/1991 | Dodwell et al. |
| 5,519,058 | A | 5/1996 | Gonick et al. |
| 5,536,412 | A | 7/1996 | Ash |
| 5,888,472 | A | 3/1999 | Bern et al. |
| 5,891,417 | A | 4/1999 | Bern et al. |
| 6,099,737 | A | 8/2000 | Sherman et al. |
| 6,332,985 | B1 | 12/2001 | Sherman et al. |
| 6,579,460 | B1 | 6/2003 | Willis et al. |
| 6,814,871 | B1 | 11/2004 | Bern et al. |
| 8,802,152 | B2 | 8/2014 | Keyser et al. |
| 8,808,750 | B2 | 8/2014 | Keyser et al. |
| 8,877,255 | B2 | 11/2014 | Keyser et al. |
| 9,033,908 | B2 | 5/2015 | Schilthuizen et al. |
| 9,457,050 | B2 | 10/2016 | Keyser et al. |
| 9,662,352 | B2 | 5/2017 | Keyser et al. |

(Continued)

FOREIGN PATENT DOCUMENTS

| | | |
|---|---|---|
| EP | 0046971 A1 | 3/1982 |
| WO | 2010101991 A1 | 9/2010 |

OTHER PUBLICATIONS

Yu, Case Studies in Environmental Medicine (CSEM) Chromium Toxicity, Agency for Toxic Substances and Disease Registry, 2008.
Faroon et al., Toxicological Profile for Cobalt, US Department of Human Services, Agency for Toxic Substances and Disease Registry, Apr. 2004.
Smith, The Role of Chelation in the Treatment of Other Metal Poisonings, J. Med. Tolicol., 9:355-369, (Oct. 2013).

(Continued)

*Primary Examiner* — John Kim
(74) *Attorney, Agent, or Firm* — Paschall & Associates, LLC; Mark Goldberg

(57) ABSTRACT

A process for removing $Co^{2+}$, $Pb^{2+}$, $Cd^{2+}$ and $Cr^{3+}$ toxins from bodily fluids is disclosed. The process involves contacting the bodily fluid with an ion exchange composition to remove the metal toxins in the bodily fluid, including blood and gastrointestinal fluid. Alternatively, blood can be contacted with a dialysis solution which is then contacted with the ion exchange composition. The ion exchange compositions are represented by the following empirical formula:

$$A_m Zr_a Ti_b Sn_c M_d Si_x O_y.$$

A composition comprising the above ion exchange compositions in combination with bodily fluids or dialysis solution is also disclosed. The ion exchange compositions may be supported by porous networks of biocompatible polymers such as carbohydrates or proteins.

12 Claims, No Drawings

(56) References Cited

U.S. PATENT DOCUMENTS

| | | |
|---|---|---|
| 9,707,255 B2 | 7/2017 | Keyser et al. |
| 9,844,567 B2 | 12/2017 | Keyser et al. |
| 9,861,658 B2 | 1/2018 | Keyser et al. |
| 9,943,637 B2 | 4/2018 | Keyser et al. |
| 10,286,390 B2 | 5/2019 | Brandts et al. |
| 2012/0226258 A1 | 9/2012 | Otto et al. |
| 2015/0225249 A1 | 8/2015 | Keyser et al. |
| 2016/0038538 A1 | 2/2016 | Keyser et al. |
| 2016/0000825 A1 | 7/2016 | Keyser et al. |
| 2016/0271174 A1 | 9/2016 | Keyser et al. |
| 2018/0214479 A1 | 8/2018 | Keyser et al. |
| 2018/0369279 A1 | 12/2018 | Frykman et al. |

OTHER PUBLICATIONS

Flora, Chelation in Metal Intoxication, International Journal of Environmental Research and Public Health, 7, 2745-2788, (2010).

Tucker, Case Studies in Environmental Medicine (CSEM) Cadmium Toxicity, Agency for Toxic Substances and Disease Registry, 2008.

Singh, A. V., et al., "Synthesis, characterization, and applications of a mew cation exchanger tamarind sulphonic acid (TSA) resin", Environmental Technology, Aug. 18, 2011, pp. 473-480, vol. 33, No. 4, Publisher: Taylor & Francis Group.

"International Preliminary Report on Patentability for PCT/US2020/040113".

Search Report and Written Opinion for 20837171.6 dated Aug. 10, 2023.

PROCESS FOR REMOVING COBALT, LEAD, CADMIUM AND CHROMIUM IONS FROM BODILY FLUIDS USING METALLATE ION EXCHANGE COMPOSITIONS

FIELD OF THE INVENTION

This invention relates to extracorporeal or intracorporeal processes for removing $Co^{2+}$, $Pb^{2+}$, $Cd^{2+}$ and $Cr^{3+}$ ions from bodily fluids. The blood or other bodily fluid is either contacted directly with a metallate ion exchange composition which is capable of selectively removing the toxins or the blood or other bodily fluid is first contacted with a dialysis solution which is then contacted with the metallate ion exchange composition.

BACKGROUND OF THE INVENTION

In mammals, e.g., humans, when the kidneys and/or liver fail to remove metabolic waste products from the body, most of the other organs of the body also soon fail. Accordingly, extensive efforts have been made to discover safe and effective methods for removing toxins from patients' blood by extracorporeal treatment of the blood. Many methods have been proposed for removing small molecular toxins, protein-bound molecules or larger molecules thought to be responsible for the coma and illness of hepatic failure. Some of these toxic compounds have been identified as urea, creatine, ammonia, phenols, mercaptans, short chain fatty acids, aromatic amino acids, false neural transmitters (octopamine), neural inhibitors (glutamate) and bile salts. Among these, phenols and mercaptans, along with bilirubin and bacterial endotoxins, also occur as strong protein-bound toxins and are thus more difficult to effectively remove from the blood. Middle molecular weight toxins having a molecular weight of about 300 to about 10,000 can also be present and are difficult to effectively remove. The art shows a number of ways to treat blood containing such toxins. The classic method is of course dialysis. Dialysis is defined as the removal of substances from a liquid by diffusion across a semipermeable membrane into a second liquid. Dialysis of blood outside of the body (hemodialysis) is the basis of the "artificial kidney." The artificial kidney treatment procedure generally used today is similar to that developed by Kolff in the early 1940s. Since the 1940s there have been several disclosures which deal with improvements on artificial kidneys or artificial livers. Thus, U.S. Pat. No. 4,261,828 discloses an apparatus for the detoxification of blood. The apparatus comprises a housing filled with an adsorbent such as charcoal or a resin and optionally an enzyme carrier. In order to prevent direct contact between the blood and the adsorbent, the adsorbent may be coated with a coating which is permeable for the substances to be adsorbed yet prevent the direct contact between the corpuscular blood components and the adsorbents. U.S. Pat. No. 4,581,141 discloses a composition for use in dialysis which contains a surface adsorptive substance, water, a suspending agent, urease, a calcium-loaded cation exchanger, an aliphatic carboxylic acid resin and a metabolizable organic acid buffer. The calcium loaded cation exchanger can be a calcium-exchanged zeolite. EP 0046971 A1 discloses that zeolite W can be used in hemodialysis to remove ammonia. Finally, U.S. Pat. No. 5,536,412 discloses hemofiltration and plasma filtration devices in which blood flows through the interior of a hollow fiber membrane and during the flow of blood, a sorbent suspension is circulated against the exterior surfaces of the hollow fiber membrane. Another step involves having the plasma fraction of the blood alternately exit and re-enter the interior of the membrane thereby effectuating removal of toxins. The sorbent can be activated charcoal along with an ion-exchanger such as a zeolite or a cation-exchange resin.

There are problems associated with the adsorbents disclosed in the above patents. For example, charcoal does not remove any water, phosphate, sodium or other ions. Zeolites have the disadvantage that they can partially dissolve in the dialysis solution, allowing aluminum and/or silicon to enter the blood. Additionally, zeolites can adsorb sodium, calcium and potassium ions from the blood thereby requiring that these ions be added back into the blood.

More recently, examples of microporous ion exchangers that are essentially insoluble in fluids, such as bodily fluids (especially blood), have been developed, namely the zirconium-based silicates and titanium-based silicates of U.S. Pat. Nos. 5,888,472; 5,891,417 and 6,579,460. The use of these zirconium-based silicate or titanium-based silicate microporous ion exchangers to remove toxic ammonium cations from blood or dialysate is described in U.S. Pat. Nos. 6,814,871, 6,099,737, and 6,332,985. Additionally, it was found that some of these compositions were also selective in potassium ion exchange and could remove potassium ions from bodily fluids to treat the disease hyperkalemia, which is discussed in patents U.S. Pat. Nos. 8,802,152; 8,808,750; 8,877,255; 9,457,050; 9,662,352; 9,707,255; 9,844,567; 9,861,658; US 2015/0225249; US 20016/0000825; US 2016/0038538; US 2016/0271174 and US 2018/0214479. Ex-vivo applications of these materials, for instance in dialysis, are described in U.S. Pat. No. 9,943,637.

Blood compatible polymers have also been incorporated into devices for treating bodily fluids. U.S. Pat. No. 9,033,908 discloses small desktop and wearable devices for removing toxins from blood. The device features a sorption filter that utilizes nano-particles embedded in a porous blood compatible polymeric matrix. Among the toxic materials targeted by this device and filter system are potassium, ammonia, phosphate, urea, and uric acid. Similarly, a 3-D printed hydrogel matrix consisting of crosslinked poly(ethylene glycol) diacrylate to which poly diacetylene-based nanoparticles are tethered proved successful for removing the toxin melittin (Nature Communications, 2014, DOI: 10.1038/ncomms4774).

Beside toxins derived from metabolic wastes, humans are susceptible to environmental toxins that may enter the body, for instance, by ingestion, absorption through the skin or inhalation. In 1997, the United States Environmental Protection Agency's Toxic Release Inventory (TRI) monitoring of 3391 large chromium processing facilities reported the release of nearly 33 million pounds of chromium to the environment. Most of this waste, 94.1%, was released to soil, including waste chromium slag containing potentially toxic levels of $Cr^{6+}$ which was used as landfill at more than 160 residential, industrial and recreational sites. Exposure routes include leaching into ground waters, dusts carried by wind and direct contact. Airborne chromium compounds accounted for 2.2% of the environmental release, including emissions from the metal industry, emissions from chromium plating facilities (almost exclusively $Cr^{6+}$ compounds) and emissions from the combustion of fuels, coal and oil. The electroplating, leather tanning and textile industries release chromium into surface waters, which accounted for about 0.3% of the total chromium release. While the tanning industry chiefly uses the less toxic $Cr^{3+}$, the plating industry almost exclusively uses $Cr^{6+}$ Exposure to $Cr^{6+}$ has been associated with lung cancer, while $Cr^{3+}$, a necessary nutrient, is toxic in large doses and has been associated with respiratory difficulties (See Agency for Toxic Substances and Disease Registry, Case Studies in Environmental Medicine (CSEM) Chromium Toxicity, Dianyl Yu, 2008). $Cr^{6+}$ is a strong oxidant and is often reduced to $Cr^{3+}$. Inhaled $Cr^{6+}$ is reduced to $Cr^{3+}$ in the lower pulmonary tract, while much of ingested $Cr^{6+}$ is reduced to $Cr^{3+}$ by gastrointestinal fluids. Airborne $Cr^{6+}$ can be similarly reduced to $Cr^{3+}$ by pollutants and $Cr^{6+}$ released to environmental waters may be reduced by waterborne organic materials to $Cr^{3+}$. Hence, elevated levels of $Cr^{3+}$ in bodily fluids may result from such exposures. Hip replacement patients sometimes experience toxic levels of $Cr^{3+}$ and $Co^{2+}$ in the blood.

Another well-known toxic metal is lead. For many years, lead was a key component of gasoline in the form of tetraethyl lead and a key component of paints. Currently lead is no longer used or rarely used in these industries, but there are still environmental dangers. Remodeling activities on old homes painted with lead-containing paints produce dusts that may be inhaled or end up in nearby soils and where lead is leached away in ground water or taken up by plants. Unreliable or unregulated water supplies represent a dangerous exposure to $Pb^{2+}$ toxicity, most notably the recent case in Flint, Michigan, USA, in which some residents were found to have dangerously high $Pb^{2+}$ levels in their blood after exposure to a new city water supply source. Lead contamination is associated with many ill health effects, including affecting the nervous and urinary systems and inducing learning and developmental disabilities in exposed children. Removal of lead from the blood of afflicted patients would reduce further exposure and damage.

Cadmium occurs naturally in association with zinc and is released into the environment during zinc mining and smelting operations, the latter of which releases cadmium-containing airborne particles. Another source of airborne cadmium comes from the incineration of municipal wastes, which contain plastics and Ni—Cd batteries. Industrial processes that use and may release cadmium to the environment include manufacture of Ni—Cd batteries, plastics with cadmium stabilizer, metal plating, and pigments. Zinc mining operations can contaminate local water sources with cadmium. In one such instance, use of the contaminated water to irrigate fields led to contamination of the rice crop and poisoning of a portion of the population (See Agency for Toxic Substances and Disease Registry, Case Studies in Environmental Medicine (CSEM) Cadmium Toxicity, Pamela G. Tucker, 2008). The primary source of cadmium exposure for the general public is dietary, while those with occupational exposure to Cd, which is primarily by inhalation, run higher risks of experiencing adverse effects. Chronic exposure to cadmium primarily affects the kidneys and secondarily the bones. Treatments for cadmium exposure largely involve removal of the patient from exposure.

Like many other metals, cobalt is released into the environment during mining and smelting operations. Application of cobalt-containing sludges or phosphate fertilizers also leads to spread of cobalt through the environment. Exposure to cobalt is more likely to occur through the diet vs. drinking water or inhalation. Cobalt is required for human health especially as a component of vitamin B12 and has been used to stimulate red blood cell production in pregnant women. However, workers exposed to higher levels of cobalt have developed respiratory problems. Cardiomyopathy in humans and animals has been reported after exposure to cobalt. Workers at nuclear facilities and nuclear waste storage sites may be exposed to potentially high levels of radioactive $^{60}Co$. (See Toxicological Profile for Cobalt, US Department of Health and Human Services, Agency for Toxic Substances and Disease Registry, April 2004).

Chelation therapy has been used to try to remove some of these metal toxins from blood. Chelation therapy directed toward removal $Co^{2+}$, $Cr^{3+}$ and $Cd^{2+}$ gave uninterpretable results or provided no benefit (J Med Toxicol., (2013) 9, 355-369). Chelation therapy has also been used for $Pb^{2+}$ poisoning. The chelating agent $CaNa_2EDTA$ has been used to remove $Pb^{2+}$ from blood, but this complex is poorly adsorbed by the gastrointestinal tract and often must be administered intravenously. It was observed that this chelate could mobilize $Pb^{2+}$, transferring it to other tissues, including the brain (Int. J. Environ. Res. Public Health, (2010), 7, 2745-2788). Dimercaptosuccinic acid (DMSA) was recognized as an antidote for heavy metal poisoning and has been used to treat $Co^{2+}$, $Cd^{2+}$ and $Pb^{2+}$ poisoning (See U.S. Pat. No. 5,519,058). Concerns about chelation therapy include toxic side effects, non-selective binding of metals, and spread of toxins through the body. Supported chelating agents, i.e., chelating agents bound to resins have been used for heavy metal removal in a dialysis mode, where the blood is on one side of a semi-permeable membrane and the resin-supported chelates on the other side (See U.S. Pat. No. 4,612,122).

Zeolites have been proposed for treating chronic lead poisoning, taken in pill form in US 20180369279A1, but zeolites have limited stability, especially in the gastrointestinal tract.

Applicants have developed a process which uses metallate ion exchangers which are essentially insoluble in fluids, such as bodily fluids (especially blood) or dialysis solutions. These ion exchangers have an empirical formula on an anhydrous basis of:

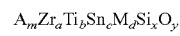

$$A_m Zr_a Ti_b Sn_c M_d Si_x O_y,$$

where A is an exchangeable cation selected from the group consisting of potassium ion, sodium ion, rubidium ion, cesium ion, calcium ion, magnesium ion, hydronium ion or mixtures thereof, M is at least one framework metal selected from the group consisting of hafnium (4+) or niobium (5+), "m" is the mole ratio of A to total metal (total metal=Zr+ Ti+Sn+M) and has a value from 0.10 to 15, "a" is the mole fraction of total metal that is Zr and has a value from zero to 1, "b" is the mole fraction of total metal that is Ti and has a value from zero to 1, "c" is the mole fraction of total metal that is Sn and has a value from zero to 1, "d" is the mole fraction of total metal that is M and has a value from zero to less than 1, where a+b+c+d=1 and a+b+c>0, "x" is the mole ratio of Si to total metal and has a value from about 0 to about 12, and "y" is the mole ratio of O to total metal and has a value from 2.1 to about 33. Since these compositions are essentially insoluble in bodily fluids (at neutral and mildly acidic or basic pH), they can be orally ingested in order to remove toxins in the gastrointestinal system as well as used to remove toxins from blood, specifically, $Co^{2+}$, $Pb^{2+}$, $Cd^{2+}$ and $Cr^{3+}$.

SUMMARY OF THE INVENTION

As stated, this invention relates to a process for removing $Co^{2+}$, $Pb^{2+}$, $Cd^{2+}$, $Cr^{3+}$ or combinations thereof from fluids selected from the group consisting of a bodily fluid, a dialysate solution and mixtures thereof, the process comprising contacting the fluid containing the toxins with an ion exchanger resulting in an ion exchanged ion exchanger thereby removing the toxins from the fluid, the metallate ion exchanger selected from zirconium metallate, titanium metallate, tin metallate, a multinary metallate containing at least two or more of zirconium, titanium or tin, or mixtures thereof, the composite metallate having an empirical formula on an anhydrous basis of:

$$A_m Zr_a Ti_b Sn_c M_d Si_x O_y$$

where A is an exchangeable cation selected from the group consisting of potassium ion, sodium ion, rubidium ion, cesium ion, calcium ion, magnesium ion, hydronium ion or mixtures thereof, M is at least one framework metal selected from hafnium (4+) or niobium (5+), "m" is the mole ratio of A to total metal (total metal=Zr+Ti+Sn+M) and has a value from 0.10 to 15, "a" is the mole fraction of total metal that is Zr and has a value from zero to 1, "b" is the mole fraction of total metal that is Ti and has a value from zero to 1, "c" is the mole fraction of total metal that is Sn and has a value from zero to 1, "d" is the mole fraction of total metal that is M and has a value from zero to less than 1, where a+b+c+d=1 and a+b+c>0, "x" is the mole ratio of Si to total metal and has a value from 0 to 12, and "y" is the mole ratio of 0 to total metal and has a value from 2.1 to 33. The bodily fluids that are treated by the present invention include blood and gastrointestinal fluids. Blood may include whole blood, blood plasma or other components of blood as known to one of skill in the art.

Another embodiment of the invention is a combination of a bodily fluid or dialysate solution and a metallate ion exchanger selected from zirconium metallate, titanium metallate, tin metallate, a multinary metallate containing at least two or more of zirconium, titanium or tin, or mixtures thereof, the composite metallate having an empirical formula on an anhydrous basis of:

$$A_m Zr_a Ti_b Sn_c M_d Si_x O_y$$

where A is an exchangeable cation selected from the group consisting of potassium ion, sodium ion, rubidium ion, cesium ion, calcium ion, magnesium ion, hydronium ion or mixtures thereof, M is at least one framework metal selected from the group consisting of hafnium (4+) or niobium (5+), "m" is the mole ratio of A to total metal (total metal=Zr+Ti+Sn+M) and has a value from 0.10 to 15, "a" is the mole fraction of total metal that is Zr and has a value from zero to 1, "b" is the mole fraction of total metal that is Ti and has a value from zero to 1, "c" is the mole fraction of total metal that is Sn and has a value from zero to 1, "d" is the mole fraction of total metal that is M and has a value from zero to less than 1, where a+b+c+d=1 and a+b+c>0, "x" is the mole ratio of Si to total metal and has a value from 0 to 12, and "y" is the mole ratio of 0 to total metal and has a value from 2.1 to 33.

Another embodiment of the invention is an apparatus incorporating a metallate ion exchanger selected from zirconium metallate, titanium metallate, tin metallate, a multinary metallate containing at least two or more of zirconium, titanium or tin, or mixtures thereof, the composite metallate having an empirical formula on an anhydrous basis of:

$$A_m Zr_a Ti_b Sn_c M_d Si_x O_y$$

where A is an exchangeable cation selected from the group consisting of potassium ion, sodium ion, rubidium ion, cesium ion, calcium ion, magnesium ion, hydronium ion or mixtures thereof, M is at least one framework metal selected from the group consisting of hafnium (4+) or niobium (5+), "m" is the mole ratio of A to total metal (total metal=Zr+Ti+Sn+M) and has a value from 0.10 to 15, "a" is the mole fraction of total metal that is Zr and has a value from zero to 1, "b" is the mole fraction of total metal that is Ti and has a value from zero to 1, "c" is the mole fraction of total metal that is Sn and has a value from zero to 1, "d" is the mole fraction of total metal that is M and has a value from zero to less than 1, where a+b+c+d=1 and a+b+c>0, "x" is the mole ratio of Si to total metal and has a value from 0 to 12, and "y" is the mole ratio of 0 to total metal and has a value from 2.1 to 33. The apparatus is configured to contact a bodily fluid or a dialysate solution to remove ions selected from $Co^{2+}$, $Pb^{2+}$, $Cd^{2+}$ and $Cr^{3+}$. The apparatus of the present invention that contains the above described metallate ion exchanger may be a sorption filter on a wearable device or a device that is remote to the individual. The metallate ion exchanger may be supported or embedded in a porous biocompatible matrix, including polymers and porous and mesoporous metal oxides and silicates. Natural or biopolymers such as cross-linked carbohydrates or proteins are in particular contemplated as the useful polymers for the present invention.

This and other objects and embodiments will become more clear after a detailed description of the invention.

DETAILED DESCRIPTION OF THE INVENTION

As stated, applicants have developed a new process for removing toxins from fluids selected from bodily fluids and dialysate solution. One essential element of the instant process is an ion exchanger which has a large capacity and strong affinity, i.e., selectivity for at least one or more of $Co^{2+}$, $Pb^{2+}$, $Cd^{2+}$ or $Cr^{3+}$. These compositions are identified as zirconium metallate, titanium metallate, tin metallate, multinary metallate containing at least two or more of zirconium, titanium or tin or mixtures thereof. They are further identified by their composite empirical formula (on an anhydrous basis) which is:

$$A_m Zr_a Ti_b Sn_c M_d Si_x O_y$$

The composition has a framework structure(s) composed of at least one of $ZrO_{6/n}$, $TiO_{6/n}$ or $SnO_{6/n}$ octahedral units where n=2 or 3 or both, optionally $NbO_{6/n}$ or $HfO_{6/n}$ octahedral units where n=2 or 3 or both, and optionally $SiO_2$ tetrahedral units. A is an exchangeable cation selected from the group consisting of potassium ion, sodium ion, rubidium ion, cesium ion, calcium ion, magnesium ion, hydronium ion or mixtures thereof, M is an optional octahedrally coordinated framework metal selected from the group consisting of hafnium (4+) or niobium (5+) or both, "m" is the mole ratio of A to total metal (total metal=Zr+Ti+Sn+M) and has a value from 0.10 to 15, "a" is the mole fraction of total metal that is Zr and has a value from zero to 1, "b" is the mole fraction of total metal that is Ti and has a value from zero to 1, "c" is the mole fraction of total metal that is Sn and has a value from zero to 1, "d" is the mole fraction of total metal that is M and has a value from zero to less than 1, where a+b+c+d=1 and a+b+c>0, "x" is the mole ratio of Si to total metal and has a value from about 0 to 12, and "y" is the mole ratio of 0 to total metal and has a value from 2.1 to 33.

The zirconium metallates, titanium metallates, tin metallates, multinary metallates containing two or more of zirconium, titanium or tin and mixtures thereof are prepared by a hydrothermal crystallization of a reaction mixture prepared by combining a reactive source of at least one of zirconium, titanium, or tin, optionally one or more M metal, optionally a Si source and at least one alkali metal and water. The alkali metal acts as a templating agent. Any zirconium compound, which can be hydrolyzed to zirconium oxide or zirconium hydroxide, can be used. Specific examples of these compounds include zirconium alkoxide, e.g., zirconium n-propoxide, zirconium hydroxide, zirconium acetate, zirconium oxychloride, zirconium chloride, zirconium phosphate and zirconium oxynitrate. Specific examples of titanium metal sources include, but are not limited to titanium alkoxides, titanium tetrachloride, titanium trichloride and titanium dioxide. Specific examples of tin metal include tin tetrachloride and tin isopropoxide. The sources of silica include colloidal silica, fumed silica, tetraethylorthosilicate and sodium silicate. Alkali sources include potassium hydroxide, sodium hydroxide, rubidium hydroxide, cesium hydroxide, sodium carbonate, potassium carbonate, rubidium carbonate, cesium carbonate, sodium halide, potassium halide, rubidium halide, and cesium halide. The M metals sources include the M metal oxides, alkoxides, halide salts, acetate salts, nitrate salts and sulfate salts. Specific examples of the M metal sources include, niobium isopropoxide, hydrous niobium oxide, hafnium isopropoxide, hafnium chloride, and hafnium oxychloride. Sources of hydroxide include quaternary ammonium hydroxides ROH, specific examples of which are tetramethylammonium hydroxide, hexamethonium dihydroxide, tetraethylammonium hydroxide, tetrapropylammonium hydroxide and tetrabutylammonium hydroxide. Generally, the hydrothermal process used to prepare the zirconium metallate, titanium metallate, tin metallate, multinary metallate or mixtures thereof ion exchange compositions of this invention involves forming a reaction mixture which in terms of molar ratios of the oxides is expressed by the formula:

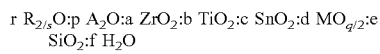

where "R" is one or more quaternary ammonium cations, "s" is the charge on the quaternary ammonium cation and is either 1 to 2, "r" has a value of 0 to 40, "p" has a value from about 0.25 to about 40, "a" has a value from about 0 to 1, "b" has a value from about 0 to 1, "c" has a value from about 0 to 1, a+b+c>0, "d" has a value from about 0 to less than 1, a+b+c+d=1, "e" has a value from 0 to 25, and "f" has a value of 10 to 3000. The reaction mixture is prepared by mixing the desired sources of zirconium, titanium or tin, optionally quaternary ammonium hydroxide, optionally silicon and optionally M metal, and alkali metal in any order to give the desired mixture. It is also necessary that the mixture have a basic pH and preferably a pH of at least 8. The basicity of the mixture is controlled by adding excess alkali hydroxide, quaternary ammonium hydroxide and/or basic compounds of the other constituents of the mixture. Having formed the reaction mixture, it is next reacted at a temperature of about 100° C. to about 200° C. for a period of about 1 to about 30 days in a sealed reaction vessel under autogenous pressure. After the allotted time, the mixture is filtered to isolate the solid product which is washed with deionized water and dried in air. As stated, the compositions of this invention have a framework structure of either octahedral $ZrO_{6/n}$ units, $TiO_{6/n}$ units, $SnO_{6/n}$ units or combinations thereof, optionally octahedral $MO_{6/n}$ units, n=2 or 3, and optionally tetrahedral $SiO_2$ units. This framework often results in a microporous structure having an intracrystalline pore system with uniform pore diameters, i.e., the pore sizes are crystallographically regular. The diameter of the pores can vary considerably from about 3 Å and larger. On the other hand, the framework of this composition may be layered or amorphous.

As synthesized, the compositions of this invention will contain some of the alkali metal templating agent in the pores, between layers or in other charge balancing positions. These metals are described as exchangeable cations, meaning that they can be exchanged with other (secondary) A' cations. Generally, the A exchangeable cations can be exchanged with A' cations selected from other alkali metal cations ($K^+$, $Na^+$, $Rb^+$, $Cs^+$), alkaline earth cations ($Mg^{2+}$, $Ca^{2+}$), hydronium ion or mixtures thereof. It is understood that the A' cation is different from the A cation. The methods used to exchange one cation for another are well known in the art and involve contacting the compositions with a solution containing the desired cation (at molar excess) at exchange conditions. Exchange conditions include a temperature of about 25° C. to about 100° C. and a time of about 20 minutes to about 2 hours. The particular cation (or mixture thereof), which is present in the final product will depend on the particular use of the composition and the specific composition being used. One specific composition is an ion exchanger where the A' cation is a mixture of $Na^+$, $Ca^{2+}$ and $H^+$ ions.

In certain instances, when a quaternary ammonium cation is used in the synthesis, usually as a hydroxide source, the quaternary ammonium cation may be incorporated into the product. Usually, this will not be the case because the quaternary ammonium cations will often be displaced by the alkali cations that have a higher affinity for incorporation into the product. However, the quaternary ammonium ion must be removed from the product. This can often be accomplished by the ion exchange processes mentioned in the previous paragraph. Sometimes the quaternary ammonium ion may be trapped in a pore and it may not be possible to remove the quaternary ammonium cation by ion exchange; a calcination will be required. Typically, a calcination consists of heating the sample to a temperature or 500-600° C. for 2-24 hours in flowing air or in flowing nitrogen followed by flowing air. In this process the quaternary ammonium cation is decomposed and replaced by a residual proton. Once the calcination is completed, the sample can be ion exchanged to the desired A' cation composition, as described above.

It is also within the scope of the invention that these ion exchange compositions can be used in powder form or can be formed into various shapes by means well known in the art. Examples of these various shapes include pills, extrudates, spheres, pellets and irregularly shaped particles. This has previously been demonstrated in U.S. Pat. Nos. 6,579,460B1 and 6,814,871B1. The ion exchange compositions of this invention may also be supported, ideally in a porous network including insertion into or binding to a blood compatible porous network such as in a sorption filter as disclosed in U.S. Pat. No. 9,033,908B2. The porous network may consist of natural or synthetic polymers and biopolymers and mesoporous metal oxides and silicates. Natural polymers (biopolymers) that are suitable may comprise a cross-linked carbohydrate or protein, made of oligomeric and polymeric carbohydrates or proteins. The biopolymer is preferably a polysaccharide. Examples of polysaccharides include α-glucans having 1,3-, 1,4- and/or 1,6-linkages. Among these, the "starch family", including amylose, amylopectin and dextrins, is especially preferred, but pullulan, elsinan, reuteran and other α-glucans, are also suitable, although the proportion of 1,6-linkages is preferably below 70%, more preferably below 60%. Other suitable polysaccharides include ß-1,4-glucans (cellulose), ß-1,3-glucans, xyloglucans, glucomannans, galactans and galactomannans (guar and locust bean gum), other gums including heterogeneous gums like xanthan, ghatti, carrageenans, alginates, pectin, ß-2,1- and ß-2,6-fructans (inulin and levan), etc. A preferred cellulose is carboxymethylcellulose (CMC, e. g. AKUCELL from AKZO Nobel). Carbohydrates which can thus be used are carbohydrates consisting only of C, H and O atoms such as, for instance, glucose, fructose, sucrose, maltose, arabinose, mannose, galactose, lactose and oligomers and polymers of these sugars, cellulose, dextrins such as maltodextrin, agarose, amylose, amylopectin and gums, e. g. guar. Preferably, oligomeric carbohydrates with a degree of polymerization (DP) from DP2 on or polymeric carbohydrates from DP50 on are used. These can be naturally occurring polymers such as starch (amylose, amylopectin), cellulose and gums or derivates hereof which can be formed by phosphorylation or oxidation. The starch may be a cationic or anionic modified starches. Examples of suitable (modified) starches that can be modified are corn-starch, potato-starch, rice-starch, tapioca starch, banana starch, and manioc starch. Other polymers can also be used (e. g. caprolactone). In certain embodiments, the biopolymer is preferably a cationic starch, most preferably an oxidized starch (for instance C6 oxidized with hypochlorite). The oxidation level may be freely chosen to suit the application of the sorbent material. Very suitably, the oxidation level is between 5 and 55%, most preferably between 25 and 35%, still more preferably between 28% and 32%. Most preferably the oxidized starch is crosslinked. A preferred cross-linking agent is di-epoxide. The crosslinking level may be freely chosen to suit the application of the sorbent material. Very suitably, the crosslinking level is between 0.1 and 25%, more preferably between 1 and 5%, and most preferably between 2.5 and 3.5%. Proteins which can be used include albumin, ovalbumin, casein, myosin, actin, globulin, hemoglobin, myoglobin, gelatin and small peptides. In the case of proteins, proteins obtained from hydrolysates of vegetable or animal material can also be used. Particularly preferred protein polymers are gelatin or a derivative of gelatin.

As stated, these compositions have particular utility in adsorbing various metal toxins, including $Co^{2+}$, $Pb^{2+}$, $Cd^{2+}$ and $Cr^{3+}$, from fluids selected from bodily fluids, dialysate solutions, and mixtures thereof. As used herein and in the claims, bodily fluids will include but not be limited to blood, blood plasma and gastrointestinal fluids. Also, the compositions are meant to be used to treat bodily fluids of any mammalian body, including but not limited to humans, cows, pigs, sheep, monkeys, gorillas, horses, dogs, etc. The instant process is particularly suited for removing toxins from a human body. There are a number of means for directly or indirectly contacting the fluids with the desired ion exchanger and thus, remove the toxins. One technique is hemoperfusion, which involves packing the above described ion exchange composition into a column through which blood is flowed. One such system is described in U.S. Pat. No. 4,261,828. As stated in the '828 patent, the ion exchange composition is preferably formed into desired shapes such as spheres. Additionally, the ion exchange composition particles can be coated with compounds, such as cellulose derivatives, which are compatible with the blood but nonpermeable for corpuscular blood components. In one specific case, spheres of the desired ion exchange compositions described above can be packed into hollow fibers thereby providing a semipermeable membrane. It should also be pointed out that more than one type of ion-exchange composition can be mixed and used in the process to enhance the efficiency of the process.

Another way of carrying out the process is to prepare a suspension or slurry of the molecular sieve adsorbent by means known in the art such as described is U.S. Pat. No. 5,536,412. The apparatus described in the '412 patent can also be used to carry out the process. The process basically involves passing a fluid, e.g. blood, containing the metal toxins through the interior of a hollow fiber and during said passing, circulating a sorbent suspension against the exterior surfaces of the hollow fiber membrane. At the same time, intermittent pulses of positive pressure are applied to the sorbent solution so that the fluid alternately exits and reenters the interior of the hollow fiber membrane thereby removing toxins from the fluid.

Another type of dialysis is peritoneal dialysis. In peritoneal dialysis, the peritoneal cavity or the abdominal cavity (abdomen) is filled via a catheter inserted into the peritoneal cavity with a dialysate fluid or solution which contacts the peritoneum. Toxins and excess water flow from the blood through the peritoneum, which is a membrane that surrounds the outside of the organs in the abdomen, into the dialysate fluid. The dialysate remains in the body for a time (dwell time) sufficient to remove the toxins. After the required dwell time, the dialysate is removed from the peritoneal cavity through the catheter. There are two types of peritoneal dialysis. In continuous ambulatory peritoneal dialysis (CAPD), dialysis is carried out throughout the day. The process involves maintaining the dialysate solution in the peritoneal cavity and periodically removing the spent dialysate (containing toxins) and refilling the cavity with a fresh dialysate solution. This is carried out several times during the day. The second type is automated peritoneal dialysis or APD. In APD, a dialysate solution is exchanged by a device at night while the patient sleeps. In both types of dialyses, a fresh dialysate solution must be used for each exchange.

The zirconium metallates, titanium metallates, tin metallates or multinary metallates of the present invention can be used to regenerate the dialysate solutions used in peritoneal dialysis, thereby further decreasing the amount of dialysate that is needed to cleanse the blood and/or the amount of time needed to carry out the exchange. This regeneration is carried out by any of the means described above for conventional dialysis. For example, in an indirect contacting process, the dialysate from the peritoneal cavity, i.e. first dialysate which has taken up metal toxins transferred across the peritoneum is now contacted with a membrane and a second dialysate solution and metal toxins are transferred across a membrane, thereby purifying the first dialysate solution, i.e. a purified dialysate solution. The second dialysate solution containing the metal toxins is flowed through at least one adsorption bed containing at least one of the ion exchangers described above, thereby removing the metal toxins and yielding a purified second dialysate solution. It is usually preferred to continuously circulate the second dialysate solution through the adsorbent bed until the toxic metal ions have been removed, i.e., $Co^{2+}$, $Pb^{2+}$, $Cd^{2+}$ and $Cr^{3+}$. It is also preferred that the first dialysate solution be circulated through the peritoneal cavity, thereby increasing the toxic metal removal efficiency and decreasing the total dwell time.

A direct contacting process can also be carried out in which the first dialysate solution is introduced into the peritoneal cavity and then flowed through at least one bed containing at least one ion exchanger. As described above, this can be carried out as CAPD or APD. The composition of the dialysate solution can be varied in order to ensure a proper electrolyte balance in the body. This is well known in the art along with various apparatus for carrying out the dialysis.

The zirconium metallates, titanium metallates, tin metallates and multinary metallates can also be formed into pills or other shapes which can be ingested orally and pick up toxins in the gastrointestinal fluid as the ion exchanger passes through the intestines and is finally excreted. In order to protect the ion exchangers from the high acid content in the stomach, the shaped articles may be coated with various coatings which will not dissolve in the stomach, but dissolve in the intestines.

As has also been stated, although the instant compositions are synthesized with a variety of exchangeable cations ("A"), it is preferred to exchange the cation with secondary cations (A') which are more compatible with blood or do not adversely affect the blood. For this reason, preferred cations are sodium, calcium, hydronium and magnesium. Preferred compositions are those containing sodium and calcium or sodium, calcium and hydronium ions. The relative amount of sodium and calcium can vary considerably and depends on the composition and the concentration of these ions in the blood.

The x-ray patterns presented in the following examples were obtained using standard x-ray powder diffraction techniques. The radiation source was a high-intensity, x-ray tube operated at 45 kV and 35 mA. The diffraction pattern from the copper K-alpha radiation was obtained by appropriate computer-based techniques. Flat compressed powder samples were continuously scanned at 2° to 56° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In the x-ray patterns reported, the relative intensities of the d-spacings are indicated by the notations vs, s, m, and w which represent very strong, strong, medium, and weak, respectively. In terms of 100× $I/I_o$, the above designations are defined as:

w>0-15; m>15-60; s>60-80 and vs>80-100

In certain instances, the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the instant invention, the following examples are set forth. It is to be understood that the examples are only by way of illustration and are not intended as an undue limitation on the broad scope of the invention as set forth in the appended claims.

EXAMPLES

Na$^+$ Ion-Exchange Procedure

The products disclosed in the following examples not synthesized in the Na$^+$ form were sodium ion-exchanged prior to testing. Typically, a three-stage ion-exchange with NaCl was employed. The ion-exchange procedure consisted of exposing 5-10 g of product to be tested to 500 mL of 1-2 M NaCl exchange solution. Three ion-exchanges were performed at 75° C., stirring for 1.5 hours for each exchange step. Exchanged solids were isolated via filtration or centrifugation.

Acid Treatment Procedure

Several of the test candidates were selected to undergo an acid treatment. A 5 wt. % nitric acid solution was used targeting 2-3 g test material in 100 g exchange solution. The acid wash was performed in a three-stage exchange procedure at 75° C. for 1.5 hours each stage. Exchanged materials were isolated via filtration, washed thoroughly with deionized water and dried at 80° C.

Example 1

In a Teflon beaker equipped with a high-speed stirrer, 101.64 g KOH (87.8%) was dissolved in 191.03 g deionized water. To this solution, added 79.64 g colloidal silica (Ludox AS-40, 40% $SiO_2$) in a single pour with vigorous stirring forming a translucent solution which turned clear after 2 hours of homogenization. To the clear solution, 77.69 g Ti(OiPr)$_4$ (97%) was added dropwise over 6 minutes. The reaction mixture turned to a white, opaque colloidal-like suspension with an additional 20 minutes of stirring. The reaction mixture was loaded into a 600 cc stirred autoclave and digested 120 hours at 175° C. stirring at 250 rpm. The solid products were isolated by centrifugation, washed with deionized water and dried at room temperature. The product was identified as titanium silicate pharmacosiderite via powder x-ray diffraction, accompanied by a slight $K_2TiSi_3O_9$ impurity. Representative x-ray diffraction lines for the product are shown in Table 1, with asterisks indicating peaks associated with the $K_2TiSi_3O_9$ impurity. Elemental analysis yielded the empirical formula $K_{1.75}TiSi_{1.06}O_{5.0}$. A portion of this product was ion-exchanged with NaCl prior to testing.

TABLE 1

| 2-Θ | d(Å) | I/I$_0$ % |
|---|---|---|
| 11.68 | 7.57 | vs |
| 15.70 | 5.64 | w* |
| 16.42 | 5.39 | w |
| 20.08 | 4.42 | w |
| 23.18 | 3.83 | m |
| 26.18 | 3.40 | w* |
| 28.40 | 3.14 | vs |
| 30.73 | 2.91 | w |
| 32.06 | 2.79 | w* |
| 32.92 | 2.72 | m |
| 34.83 | 2.57 | w |
| 36.84 | 2.44 | m |
| 38.81 | 2.32 | w |
| 40.38 | 2.23 | w* |
| 40.56 | 2.22 | w |
| 47.08 | 1.93 | w |
| 48.43 | 1.88 | m |
| 50.03 | 1.82 | w |

*$K_2TiSi_3O_9$ impurity

Example 2

In a Teflon beaker equipped with a high-speed stirrer, 73.34 g KOH (87.7%) was dissolved in 254.43 g deionized water. To this solution, 68.27 g colloidal silica (Ludox AS-40, 40% $SiO_2$) was added over 10 minutes with vigorous stirring, forming a white suspension. After 20 minutes of homogenization, 45.61 g zirconium acetate solution (22.1% $ZrO_2$) was added fast dropwise. After 10 minutes of homogenization, 5.35 g hydrous $Nb_2O_5$ (62.5%) was added and the reaction mixture was stirred for an additional 5 minutes. The reaction mixture was loaded into a 600 cc stirred autoclave and digested for 24 hours at 200° C. stirring at 250 RPM. The solid product was isolated by centrifugation, washed with deionized water and dried in air. X-ray powder diffraction revealed the product to have the umbite structure. Representative diffraction lines for the product are shown below in Table 2. Elemental analysis yielded the empirical formula $K_{2.15}Zr_{0.81}Nb_{0.19}Si_{3.34}O_{9.5}$. A portion of product was ion-exchanged with NaCl before use in testing.

TABLE 2

| 2-Θ | d(Å) | I/I₀ % |
|---|---|---|
| 10.82 | 8.17 | m |
| 13.32 | 6.64 | m |
| 14.90 | 5.94 | s |
| 16.34 | 5.42 | w |
| 17.00 | 5.21 | w-m |
| 18.08 | 4.90 | w |
| 20.02 | 4.43 | w-m |
| 21.78 | 4.08 | m |
| 24.54 | 3.63 | w |
| 25.03 | 3.56 | w |
| 26.40 | 3.37 | m |
| 28.38 | 3.14 | m |
| 28.96 | 3.08 | m |
| 29.50 | 3.03 | vs |
| 29.96 | 2.98 | s |
| 30.76 | 2.90 | m |
| 31.84 | 2.81 | w |
| 32.96 | 2.72 | w |
| 34.14 | 2.62 | w |
| 34.94 | 2.57 | w-m |
| 37.62 | 2.39 | w |
| 38.10 | 2.36 | w |
| 41.52 | 2.17 | w |
| 42.56 | 2.12 | w |
| 43.22 | 2.09 | w |
| 45.58 | 1.99 | w |
| 46.06 | 1.97 | w |
| 48.74 | 1.87 | w |
| 49.74 | 1.83 | w |
| 50.22 | 1.82 | m |

Example 3

A Teflon beaker was charged with 650.00 g TEAOH (35%) and stirred with a high-speed stirrer. Next, 53.05 g TEOS (98%) was added fast dropwise with stirring. The reaction mixture was stirred for an hour to hydrolyze the TEOS, resulting in a clear solution. Then 12.76 g $SnCl_4$*5 $H_2O$ was dissolved in 25.00 g deionized water. This solution was added slow dropwise to the reaction mixture over a period of 40 minutes. The reaction mixture was stirred vigorously for an additional 20 minutes and then placed in a Teflon bottle and stirred overnight. The next day $Na^+$ was added; 4.17 g NaCl was dissolved in 15.00 g deionized water and was added to the reaction mixture in a dropwise fashion. As the addition proceeded, the previously clear solution gave way to a cloudy suspension. The reaction mixture was transferred to a Teflon bottle and digested at 100° C. for 4 days. The solid product was isolated by centrifugation, washed with deionized water and dried at room temperature. Characterization by powder x-ray diffraction showed the Na—Sn-Silicate to be amorphous. A portion of product was ion-exchanged with NaCl before use in testing.

Example 4

A sodium nonatitanate, $Na_4Ti_9O_{20}$, received from Honeywell was employed. Characterization of the sample by powder x-ray diffraction was consistent with sodium nonatitanate. Representative x-ray diffraction lines for the sample are given in Table 3 below.

TABLE 3

| 2-Θ | d(Å) | I/I₀ % |
|---|---|---|
| 9.00 | 9.81 | vs |
| 18.08 | 4.90 | w |
| 24.38 | 3.65 | w |
| 24.40 | 3.65 | w |
| 28.12 | 3.17 | w |
| 29.01 | 3.08 | w |
| 33.83 | 2.65 | w |
| 34.70 | 2.58 | w |
| 39.94 | 2.26 | w |
| 44.33 | 2.04 | w |
| 44.63 | 2.03 | w |
| 47.70 | 1.91 | w-m |
| 48.34 | 1.88 | w-m |

Example 5

A solution was prepared by dissolving 40.69 g NaOH pellets (Fisher) in 1141.37 g deionized water. With vigorous overhead stirring using a high-speed mechanical stirrer (600 rpm), 68.79 g of colloidal silica (Ludox™ AS-40; 40% $SiO_2$) was added slowly but with a single pour. After about an hour of mixing, 149.15 g of $Ti(OiPr)_4$ (97%) was added quickly via a single pour to the colloidal translucent suspension immediately causing precipitate formation. The reaction mixture was homogenized for an additional 5 minutes and loaded into a Parr 2 L stirred autoclave. The reaction mixture was digested for 24 hours at 200° C. while stirring at 300 rpm, including a 4 hour heat-up from room temperature to 200° C. The product was isolated and washed 3 times with deionized water using centrifugation and dried in a 100° C. oven overnight. The product was characterized by powder X-ray diffraction, exhibiting both zorite and sitinakite components. Representative diffraction lines for the product are shown in Table 4, Example 5A. The described procedure was repeated to produce a duplicate sample, the representative diffraction lines for this material are shown in Table 4, Example 5B.

TABLE 4

| Example 5A | | | Example 5B | | |
|---|---|---|---|---|---|
| 2-Θ | d(Å) | I/I₀ % | 2-Θ | d(Å) | I/I₀ % |
| 7.66 | 11.54 | m | 7.72 | 11.44 | s |
| 11.26 | 7.85 | vs | 11.38 | 7.77 | vs |
| 12.72 | 6.95 | m | 12.88 | 6.87 | m |
| 16.85 | 5.26 | w | 16.96 | 5.22 | m |
| 19.90 | 4.46 | w | 17.74 | 5.00 | w |
| 25.94 | 3.43 | m | 18.28 | 4.85 | m |
| 26.38 | 3.38 | m | 20.05 | 4.43 | w |
| 28.98 | 3.08 | w-m | 24.85 | 3.58 | w |
| 29.20 | 3.06 | m | 26.11 | 3.41 | w |
| 29.96 | 2.98 | m | 26.54 | 3.36 | m |
| 32.37 | 2.76 | w | 28.09 | 3.18 | w |
| 34.64 | 2.59 | m | 29.14 | 3.06 | m |

TABLE 4-continued

| Example 5A | | | Example 5B | | |
|---|---|---|---|---|---|
| 2-Θ | d(Å) | I/I$_0$ % | 2-Θ | d(Å) | I/I$_0$ % |
| | | | 29.34 | 3.04 | m-s |
| | | | 30.06 | 2.97 | m |
| | | | 30.91 | 2.89 | m |
| | | | 32.54 | 2.75 | m |
| | | | 34.18 | 2.62 | m |
| | | | 34.56 | 2.59 | m |
| | | | 34.74 | 2.58 | s-vs |
| | | | 37.10 | 2.42 | w |
| | | | 48.12 | 1.89 | m |

Example 6

A solution was prepared by dissolving 29.07 g NaOH pellets (Fisher) in 815.27 g deionized water. With vigorous overhead stirring using a high-speed mechanical stirrer, 49.13 g colloidal silica (Ludox™ AS-40, 40% SiO$_2$) was added slowly but with a single pour. After about an hour of mixing, 106.53 g of Ti(OiPr)$_4$ (97%) was added quickly via a single pour to the colloidal translucent suspension immediately forming a precipitate. The reaction mixture was homogenized for an additional 5 minutes and loaded into a 2 L autoclave. The material was digested for 24 hours at 200° C. under static conditions. The product was isolated by centrifugation, washed 3 times with deionized water and dried in a 100° C. oven overnight. The product was characterized by X-ray diffraction, which identified the product as titanium silicate sitinakite. Representative x-ray diffraction lines for the product are shown in Table 5.

TABLE 5

| 2-Θ | d(Å) | I/I$_0$ % |
|---|---|---|
| 11.30 | 7.82 | vs |
| 17.85 | 4.97 | w |
| 26.68 | 3.34 | w |
| 27.25 | 3.27 | m |
| 27.68 | 3.22 | m-s |
| 32.30 | 2.77 | w |
| 34.50 | 2.60 | m |

Example 7

A series of sodium tin silicates were prepared as follows. To a Teflon beaker, 36.16 g colloidal silica (Ludox AS-40, 40% SiO$_2$) was added and placed under a high-speed stirrer. Then a solution was prepared by dissolving 19.26 g NaOH pellets in 90.00 g deionized water. This solution was added to the colloidal silica with vigorous stirring. The white reaction mixture was homogenized for 20 minutes post-addition. Separately, 21.10 g SnCl$_4$*5H$_2$O was dissolved in 83.48 g deionized water. This solution was added to the reaction mixture and mixed for an additional 20 minutes. The thin, white reaction mixture was split among four 125 mL Teflon-lined autoclaves and digested under static conditions at 200° C. for 3, 7, 14 and 21 days at autogenous pressures. The solid products were isolated via centrifugation, washed with deionized water and dried at room temperature. Powder X-ray diffraction was used to characterize the products. Representative x-ray diffraction lines are shown for the products in Table 6.

TABLE 6

| Example 7A, 3 days | | | Example 7B, 7 days | | | Example 7C, 14 days | | | Example 7D, 21 days | | |
|---|---|---|---|---|---|---|---|---|---|---|---|
| 2-Θ | d(Å) | I/I$_0$ % | 2-Θ | d(Å) | I/I$_0$ % | 2-Θ | d(Å) | I/I$_0$ % | 2-Θ | d(Å) | I/I$_0$ % |
| 7.42 | 11.91 | s-vs | 7.46 | 11.84 | w | 7.52 | 11.74 | m | 7.58 | 11.65 | w-m |
| 11.12 | 7.95 | w-m | 14.10 | 6.28 | m | 14.04 | 6.30 | m | 14.06 | 6.29 | m |
| 18.88 | 4.70 | m | 15.25 | 5.81 | m | 15.22 | 5.82 | m-s | 15.26 | 5.80 | m |
| 32.21 | 2.78 | vs | 16.04 | 5.52 | m | 16.00 | 5.54 | m | 16.02 | 5.53 | m |
| 34.35 | 2.61 | m | 17.19 | 5.15 | w | 17.16 | 5.16 | w-m | 17.17 | 5.16 | m |
| 43.02 | 2.10 | m | 18.82 | 4.71 | w | 18.78 | 4.72 | w | 18.82 | 4.71 | w |
| | | | 20.84 | 4.26 | w | 20.78 | 4.27 | w-m | 20.80 | 4.27 | m |
| | | | 22.46 | 3.96 | w | 22.36 | 3.97 | w | 22.38 | 3.97 | w |
| | | | 27.02 | 3.30 | w | 23.66 | 3.76 | w | 27.00 | 3.30 | m |
| | | | 27.19 | 3.28 | w | 27.04 | 3.30 | m | 28.22 | 3.16 | w |
| | | | 29.38 | 3.04 | vs | 28.20 | 3.16 | w | 29.36 | 3.04 | vs |
| | | | 30.76 | 2.90 | m | 29.34 | 3.04 | vs | 30.76 | 2.90 | m |
| | | | 32.32 | 2.77 | m | 30.74 | 2.91 | m | 32.32 | 2.77 | m |
| | | | 32.67 | 2.74 | w | 32.28 | 2.77 | m | 34.00 | 2.63 | w |
| | | | 34.76 | 2.58 | w | 33.92 | 2.64 | m | 34.70 | 2.58 | w |
| | | | 36.77 | 2.44 | m | 34.68 | 2.58 | m | 36.74 | 2.44 | m |
| | | | 38.14 | 2.36 | w-m | 36.74 | 2.44 | w-m | 38.34 | 2.35 | w-m |
| | | | 38.34 | 2.35 | w-m | 38.07 | 2.36 | m | 41.66 | 2.17 | w |
| | | | 43.84 | 2.06 | w | 38.36 | 2.34 | w-m | 43.77 | 2.07 | m |
| | | | 48.66 | 1.87 | m | 41.35 | 2.18 | w | 45.64 | 1.99 | w |
| | | | | | | 41.66 | 2.17 | w | 46.88 | 1.94 | w |
| | | | | | | 43.76 | 2.07 | w | 48.06 | 1.89 | w |
| | | | | | | 48.60 | 1.87 | m | 48.66 | 1.87 | m |
| | | | | | | 49.24 | 1.85 | w | 49.34 | 1.85 | w |
| | | | | | | 49.72 | 1.83 | w | 49.78 | 1.83 | w |

Example 8

A Teflon beaker equipped with a high-speed stirrer, was charged with 42.61 g colloidal silica (Ludox AS-40, 40% $SiO_2$). A solution was prepared by dissolving 29.28 g NaOH pellets in 163.38 g deionized water. This solution was added fast dropwise to the colloidal silica with vigorous stirring, forming a creamy, brilliant white reaction mixture. Separately, a solution was prepared by dissolving 14.73 g $SnCl_4*5H_2O$ in 200 g deionized water. This solution was added in a single pour with vigorous stirring. The brilliant white reaction mixture was stirred for an additional 20 minutes. The homogenous white gel was loaded into a 600 cc stirred autoclave and digested for 72 hours at 200° C., stirred at 250 rpm. The solid products were isolated by centrifugation, washed with deionized water and dried at room temperature. Powder X-ray diffraction identified the product as SnSi-1. Representative x-ray diffraction lines are shown in Table 7. Elemental analysis yielded the empirical formula $Na_{4.45}SnSi_{4.13}O_{12.5}$.

TABLE 7

| 2-Θ | d(Å) | $I/I_0$ % |
|---|---|---|
| 7.04 | 12.55 | s-vs |
| 7.72 | 11.44 | m |
| 10.88 | 8.12 | w |
| 14.16 | 6.25 | w |
| 16.27 | 5.44 | w |
| 18.97 | 4.68 | w-m |
| 21.21 | 4.19 | w |
| 23.46 | 3.79 | w |
| 24.50 | 3.63 | w |
| 31.86 | 2.81 | s |
| 32.54 | 2.75 | vs |
| 42.99 | 2.10 | w |
| 43.25 | 2.09 | w |

Example 9

In a Teflon beaker, 19.54 g KOH (85.22%) was dissolved in 115.86 g deionized water using a Heidolph stirrer. Then 46.14 g colloidal silica (LUDOX AS-40, 40% $SiO_2$) was added in a single pour and allowed to stir for 10 minutes. This was followed by the addition of 30.0 g $Ti(OiPr)_4$ (97%). A brilliant white gel resulted which was allowed to homogenize further. The homogenous gel was distributed among three Teflon-lined Parr reactors and digested quiescently at a temperature of 200° C. for 46 hr at autogenous pressure. The solid products were isolated by centrifugation, washed with de-ionized water and dried at room temperature. The product was identified as Ti-umbite by powder x-ray diffraction. Representative diffraction lines are shown in Table 8 below. Elemental analysis yielded the empirical composition $K_{1.79}TiSi_{2.60}O_{8.1}$. The products were sodium ion-exchanged before they were tested.

TABLE 8

| 2-Θ | d(Å) | $I/I_0$ % |
|---|---|---|
| 11.26 | 7.85 | m |
| 13.72 | 6.45 | m |
| 14.20 | 6.23 | w |
| 15.33 | 5.77 | m |
| 17.92 | 4.95 | w |
| 19.21 | 4.62 | w |
| 20.60 | 4.31 | w |
| 21.83 | 4.07 | w |
| 22.49 | 3.95 | w |
| 22.90 | 3.88 | w |
| 24.96 | 3.57 | w |
| 25.76 | 3.46 | m |
| 26.51 | 3.36 | w |
| 27.44 | 3.25 | w |
| 27.89 | 3.20 | m |
| 28.54 | 3.13 | m |
| 29.80 | 3.00 | m |
| 30.34 | 2.94 | s |
| 30.62 | 2.92 | m |
| 30.88 | 2.89 | m |
| 31.66 | 2.82 | s |
| 32.56 | 2.75 | w |
| 32.94 | 2.72 | m |
| 33.82 | 2.65 | w |
| 35.42 | 2.53 | w |
| 35.84 | 2.50 | w |
| 36.50 | 2.46 | w |
| 37.74 | 2.38 | w |
| 38.44 | 2.34 | w |
| 38.64 | 2.33 | w |
| 38.92 | 2.31 | w |
| 39.10 | 2.30 | m |
| 39.58 | 2.28 | w |
| 41.32 | 2.18 | w |
| 42.12 | 2.14 | w |
| 42.72 | 2.11 | w |
| 44.50 | 2.03 | w |
| 45.05 | 2.01 | w |
| 45.86 | 1.98 | w |
| 46.32 | 1.96 | w |
| 47.07 | 1.93 | w |
| 47.71 | 1.90 | w |
| 50.27 | 1.81 | w |
| 51.06 | 1.79 | w |
| 51.84 | 1.76 | w |
| 52.38 | 1.75 | w |
| 52.68 | 1.74 | w |
| 53.30 | 1.72 | w |
| 54.62 | 1.68 | w |
| 55.40 | 1.66 | w |
| 55.58 | 1.65 | w |

Example 10

A Teflon beaker under a high-speed stirrer was charged with 69.15 g colloidal silica (Ludox AS-40, 40% $SiO_2$). A solution was prepared by dissolving 74.25 g KOH (87.7%) in 257.16 g deionized water. This solution was added to the colloidal silica in a single pour with vigorous stirring, forming a white suspension that turned clear after 20 minutes of homogenization. To the clear solution, 49.45 g of zirconium acetate solution (22.1 wt % $ZrO_2$) was added fast dropwise and the reaction mixture allowed to homogenize. The reaction mixture was loaded into a 600 cc stirred autoclave and digested for 36 hours at 200° C., stirring at 250 rpm. The solid product was isolated by centrifugation, washed with water, and dried at room temperature. The product was identified as Zr-umbite via powder x-ray diffraction. Representative x-ray diffraction lines are shown in Table 9. Elemental analysis yielded the empirical composition $K_{2.33}ZrSi_{3.47}O_{10.1}$. A portion of product was ion-exchanged with NaCl before testing.

TABLE 9

| 2-Θ | d(Å) | I/I₀ % |
|---|---|---|
| 10.92 | 8.10 | m |
| 13.40 | 6.60 | m |
| 15.02 | 5.89 | vs |
| 16.49 | 5.37 | w |
| 17.14 | 5.17 | m |
| 18.18 | 4.88 | w |
| 20.20 | 4.39 | w-m |
| 21.90 | 4.06 | m |
| 24.74 | 3.60 | w |
| 25.10 | 3.55 | w |
| 26.70 | 3.34 | m |
| 28.24 | 3.16 | w |
| 28.66 | 3.11 | m |
| 29.14 | 3.06 | m |
| 29.60 | 3.02 | vs |
| 30.24 | 2.95 | s |
| 30.98 | 2.88 | m |
| 32.08 | 2.79 | w |
| 34.38 | 2.61 | w |
| 34.90 | 2.57 | w-m |
| 35.32 | 2.54 | w |
| 41.72 | 2.16 | w |
| 43.52 | 2.08 | w |

Example 11

In a Teflon beaker placed under a high-speed stirrer, 15.39 g KOH (87.8%) was dissolved in 26.01 g deionized water. Then added 14.47 g colloidal silica (Ludox AS-40, 40% $SiO_2$) in a single pour with vigorous stirring. An initially translucent solution turned clear after 2 hours of homogenization. To the clear solution, 14.12g $Ti(OiPr)_4$ (97%) was added dropwise over 7 minutes. The reaction mixture turned to a beige, opaque colloidal-like suspension after an additional 20 minutes of stirring. The reaction mixture was loaded into a 125 mL Parr reactor and digested quiescently for 5 days at 150° C. at autogenous pressure. The solid product was isolated by centrifugation, washed with deionized water and dried at room temperature. Powder X-ray diffraction identified the product as titanium silicate pharmacosiderite. Representative diffraction lines for the product are shown in Table 10. Elemental analysis provided the empirical composition $K_{1.45}TiSi_{1.13}O_x$. A portion of the product was ion exchanged with NaCl before testing.

TABLE 10

| 2-Θ | d(Å) | I/I₀ % |
|---|---|---|
| 11.32 | 7.81 | vs |
| 16.00 | 5.53 | w |
| 19.82 | 4.48 | w |
| 22.61 | 3.93 | w |
| 27.58 | 3.23 | m |
| 28.16 | 3.17 | m |
| 32.67 | 2.74 | w |
| 34.50 | 2.60 | w |
| 36.30 | 2.47 | w |
| 38.42 | 2.34 | w |
| 46.46 | 1.95 | w |

Example 12

The alkoxides TEOS (98%), 38.00 g, and $Ti(OiPr)_4$ (97%), 10.48 g were mixed in a
Teflon beaker placed under a high-speed stirrer. Separately, 5.89 g NaOH (99%) was dissolved in 85.00 g deionized water. This solution was added rather quickly to the stirring reaction mixture, dropperwise, using a 23 ml dropper. After the addition of a few dropper volumes of NaOH solution, the addition was stopped, and the reaction mixture allowed to stir a few minutes as a gel had formed. Then addition was continued to completion. The thick gel was then stirred for 2 hr to facilitate homogenization. The reaction mixture was transferred to two Parr Teflon-lined reactors and digested at 200° C. for 140 hr, quiescently at autogenous pressure. The products were isolated by centrifugation, washed with deionized water and dried at room temperature. Characterization of the solid by powder x-ray diffraction showed the material to have the zorite topology. Representative x-ray diffraction lines for the product are given in Table 11 below.

TABLE 11

| 2-Θ | d(Å) | I/I₀ % |
|---|---|---|
| 7.62 | 11.59 | m |
| 12.72 | 6.95 | s-vs |
| 12.92 | 6.85 | m-s |
| 16.87 | 5.25 | m |
| 19.91 | 4.46 | w-m |
| 24.84 | 3.58 | m |
| 26.02 | 3.42 | m |
| 26.36 | 3.38 | m |
| 29.06 | 3.07 | m-s |
| 29.28 | 3.05 | vs |
| 29.94 | 2.98 | s |
| 30.79 | 2.90 | m |
| 32.38 | 2.76 | m |
| 34.08 | 2.63 | m |
| 34.66 | 2.59 | m |
| 35.94 | 2.50 | w |
| 36.79 | 2.44 | w |
| 37.03 | 2.43 | w |
| 39.26 | 2.29 | w |
| 39.58 | 2.28 | w |
| 41.62 | 2.17 | w |
| 41.88 | 2.16 | w |
| 42.52 | 2.12 | w |
| 43.10 | 2.10 | w |
| 44.74 | 2.02 | w |
| 46.97 | 1.93 | w |
| 48.04 | 1.89 | w |
| 48.50 | 1.88 | w |
| 50.89 | 1.79 | w |
| 51.52 | 1.77 | w |
| 52.26 | 1.75 | w |
| 52.60 | 1.74 | m |
| 53.90 | 1.70 | m |

Example 13

This manufactured sample, received from UOP, has the sitinakite structure with anhydrous composition $Na_{3.24}Ti_{2.67}Nb_{1.18}Si_2O_{1.39}$. Representative x-ray diffraction lines for this material are shown in table 12 below.

TABLE 12

| 2-Θ | d(Å) | I/I₀ % |
|---|---|---|
| 8.76 | 10.08 | w* |
| 10.00 | 8.84 | w* |
| 11.28 | 7.84 | vs |
| 14.71 | 6.02 | m |
| 15.90 | 5.55 | w |
| 17.60 | 5.03 | m |
| 18.00 | 4.92 | w* |
| 18.58 | 4.77 | w |
| 22.67 | 3.92 | w |
| 23.64 | 3.76 | w* |

TABLE 12-continued

| 2-Θ | d(Å) | I/I₀ % |
|---|---|---|
| 25.26 | 3.52 | w |
| 26.46 | 3.37 | m |
| 27.42 | 3.25 | m |
| 29.63 | 3.01 | w |
| 30.25 | 2.95 | w* |
| 31.80 | 2.81 | w |
| 32.25 | 2.77 | w |
| 33.92 | 2.64 | m |
| 34.26 | 2.62 | m |
| 36.19 | 2.48 | w |
| 36.99 | 2.43 | w |
| 37.63 | 2.39 | w |
| 42.87 | 2.11 | w |
| 44.39 | 2.04 | w |
| 45.15 | 2.01 | w |
| 45.97 | 1.97 | w |
| 46.23 | 1.96 | w |
| 46.76 | 1.94 | w |
| 47.74 | 1.90 | w |

*impurity

Example 14

This sample is that of example 13 but has been additionally acid-washed, which leads to some ion exchange, removing some sodium. The anhydrous composition is $H_xNa_{1.56}Nb_{1.14}Ti_{2.60}Si_2O_y$. Powder x-ray diffraction on this sample identified it as having the sitinakite structure. Representative diffraction lines for the material are shown in Table 13 below.

TABLE 13

| 2-Θ | d(Å) | I/I₀ % |
|---|---|---|
| 11.26 | 7.85 | vs |
| 14.76 | 6.00 | m |
| 15.94 | 5.56 | w |
| 17.62 | 5.03 | m |
| 18.56 | 4.78 | w |
| 21.81 | 4.07 | w |
| 25.29 | 3.52 | w |
| 26.44 | 3.37 | m |
| 27.14 | 3.28 | m |
| 27.48 | 3.24 | m |
| 29.76 | 3.00 | w |
| 31.94 | 2.80 | m |
| 32.19 | 2.78 | w |
| 33.10 | 2.70 | w |
| 33.94 | 2.64 | m |
| 34.22 | 2.62 | m |
| 36.14 | 2.48 | w |
| 36.88 | 2.44 | w |
| 37.44 | 2.40 | w |
| 45.32 | 2.00 | w |
| 45.94 | 1.97 | w |
| 46.18 | 1.96 | m |
| 46.82 | 1.94 | w |
| 47.64 | 1.91 | w |
| 48.38 | 1.88 | w |

Example 15

This sample has the sitinakite structure with the anhydrous composition $Na_{3.16}Ti_{2.77}Nb_{1.05}Si_2O_{13.74}$. Large batches of this material were prepared using the formulation: 0.95 Na₂O:0.15 Nb₂O₅:0.75 TiO₂:0.85 SiO₂:129 H₂O:3.0 i-PrOH:3.4 EtOH A typical preparation used 50% NaOH solution, hydrous niobium pentoxide, Titanium isopropoxide, Ti(OiPr)₄, tetraethylorthosilicate (TEOS) and deionized water. The NaOH solution was diluted with water into which the hydrous niobium pentoxide was slurried. Then TEOS was slowly added with vigorous stirring and the reaction mixture homogenized for an additional 15 minutes post-addition. Then Ti(OiPr)₄ was slowly added and the reaction mixture homogenized further. The reaction mixture was transferred to a reactor and digested at 200° C. for 24 hr at autogenous pressure. The product was isolated by filtration, washed with deionized water and dried. Representative x-ray diffraction lines for the product are shown in table 14 below.

TABLE 14

| 2-Θ | d(Å) | I/I₀ % |
|---|---|---|
| 8.75 | 10.10 | w* |
| 9.99 | 8.85 | w* |
| 11.2 | 7.85 | vs |
| 14.69 | 6.03 | m |
| 15.93 | 5.56 | w |
| 17.58 | 5.04 | m |
| 18.58 | 4.77 | w |
| 22.68 | 3.92 | w |
| 25.30 | 3.52 | w |
| 25.98 | 3.43 | w |
| 26.42 | 3.37 | m |
| 27.10 | 3.29 | w |
| 27.0 | 3.25 | m |
| 29.59 | 3.02 | w |
| 30.21 | 2.96 | w |
| 31.79 | 2.81 | w |
| 32.24 | 2.77 | w |
| 33.84 | 2.65 | m |
| 34.24 | 2.62 | m |
| 36.15 | 2.48 | w |
| 36.93 | 2.43 | w |
| 37.49 | 2.40 | w |
| 42.81 | 2.11 | w |
| 44.37 | 2.04 | w |
| 45.15 | 2.01 | w |
| 45.95 | 1.97 | w |
| 46.28 | 1.96 | w |
| 46.66 | 1.94 | w |
| 47.74 | 1.90 | w |

*impurity

Example 16

A solution was prepared by dissolving 11.31 g NaOH pellets in 20 g deionized water. To this solution, 3.59 g LiOH*H₂O (Aldrich) was added with vigorous stirring. After 20 minutes of homogenization, added 27.84 g colloidal silica (Ludox AS-40, 40% SiO₂) dropwise over 10 minutes. Separately, a solution was prepared by dissolving 16.25 g SnCl₄*5H₂O in 20.7 g H₂O. After 1 hour of homogenization, this solution was added to the white suspension and mixed for an additional 20 minutes post addition. The creamy reaction mixture was loaded into a 125 mL autoclave and digested 16 days at 200° C. quiescently at autogenous pressure. The solid product was isolated by centrifugation, washed with deionized water and dried at room temperature. The product was analyzed via powder x-ray diffraction and representative x-ray diffraction lines for the product are listed in Table 15 below. A portion of this material was sodium ion-exchanged prior to testing.

TABLE 15

| 2-Θ | d(Å) | $I/I_0$ % |
|---|---|---|
| 14.50 | 6.10 | m |
| 16.22 | 5.46 | m |
| 19.14 | 4.63 | w-m |
| 20.44 | 4.34 | w |
| 24.99 | 3.56 | w |
| 27.06 | 3.29 | m |
| 29.82 | 2.99 | vs |
| 33.22 | 2.69 | m |
| 35.62 | 2.52 | w |
| 37.10 | 2.42 | m |
| 38.82 | 2.32 | w |
| 41.90 | 2.15 | w |
| 44.54 | 2.03 | m |
| 46.98 | 1.93 | w |
| 47.56 | 1.91 | m |
| 49.46 | 1.84 | w |
| 49.83 | 1.83 | w |
| 51.56 | 1.77 | w |
| 53.86 | 1.70 | w |
| 54.36 | 1.69 | w |

Example 17

A potassium titanate sample received from Honeywell was a composite consisting of mostly potassium octatitanate, $K_2Ti_8O_{17}$, along with some potassium hexatitanate, $K_2Ti_6O_{13}$, and some anatase, $TiO_2$, was used in this study. The sample was characterized by powder x-ray diffraction. Representative x-ray diffraction lines are shown in table 16. The sample was sodium ion exchanged prior to testing.

TABLE 16

| 2-Θ | d(Å) | $I/I_0$ % |
|---|---|---|
| 11.14 | 7.94 | s |
| 11.46 | 7.72 | m-s |
| 12.04 | 7.34 | w |
| 13.82 | 6.40 | w |
| 19.77 | 4.49 | w |
| 24.10 | 3.69 | w |
| 25.30 | 3.52 | vs |
| 28.91 | 3.09 | m |
| 29.25 | 3.05 | m |
| 29.93 | 2.98 | w |
| 31.99 | 2.80 | w |
| 33.13 | 2.70 | w |
| 34.70 | 2.58 | w |
| 36.93 | 2.43 | w |
| 37.79 | 2.38 | m |
| 38.57 | 2.33 | w |
| 43.02 | 2.10 | w |
| 43.51 | 2.08 | w |
| 47.68 | 1.91 | m |
| 48.04 | 1.89 | m |
| 49.17 | 1.85 | w |
| 53.87 | 1.70 | w-m |
| 55.06 | 1.67 | w-m |

Examples 18A and 18B

A Teflon beaker was charged with 150.00 g TEAOH (35%) and began stirring with a high speed stirrer. Next, 53.05 g TEOS (98%) was added dropperwise and allowed to stir for 2 hr to hydrolyze TEOS. Separately, 11.72 g $ZrOCl_2*8H_2O$ was dissolved in 2.00 g deionized water. This solution was added to the reaction mixture in a dropwise fashion, intermittently. Over the course of the addition a white gel formed. This was homogenized further for 2 hours. A solution was prepared dissolving 14.40 g CsOAc (98%) in 2.00 g deionized water. This solution was added quickly to the reaction mixture. The reaction mixture was transferred to Teflon-lined Parr reactors and digested at 175° C. for 48 (Example 18A) and 96 hr (Example 18B). The products were isolated by centrifugation, washed with deionized water and dried in air. Powder X-ray diffraction showed the products to be amorphous. A portion of the products were sodium ion exchanged before testing.

Example 19

In a Teflon beaker under a high-speed stirrer, 22.76 g NaOH pellets was dissolved in 357.45 g deionized water. To this solution, 41.38 g colloidal silica (Ludox AS-40, 40% $SiO_2$) was added over a period of 10 minutes with vigorous stirring, forming a white suspension. After 20 minutes of homogenization, 28.44 g zirconium acetate solution (22.1 wt % $ZrO_2$) was added and contents stirred for an additional 3 minutes. The reaction mixture was loaded into a 600 cc stirred autoclave and digested for 72 hours at 200° C. while stirring at 250 RPM. The solid products were isolated by centrifugation, washed with deionized water and dried at room temperature. The product was identified as Zr-gaidonnayite via x-ray diffraction. Representative diffraction lines for the product are shown in table 17 below. Elemental analysis yielded the empirical composition $Na_{2.19}ZrSi_{3.28}O_{9.66}$.

TABLE 17

| 2-Θ | d(Å) | $I/I_0$ % |
|---|---|---|
| 13.88 | 6.37 | m |
| 15.12 | 5.86 | vs |
| 15.80 | 5.60 | m-s |
| 20.58 | 4.31 | w |
| 26.72 | 3.33 | w |
| 27.65 | 3.22 | w |
| 28.68 | 3.11 | vs |
| 30.54 | 2.93 | m-s |
| 31.18 | 2.87 | w-m |
| 31.81 | 2.81 | w-m |
| 34.10 | 2.63 | w |
| 36.12 | 2.48 | w |
| 37.46 | 2.40 | w |
| 41.14 | 2.19 | w |
| 43.12 | 2.10 | w |
| 44.59 | 2.03 | w |
| 48.00 | 1.89 | w-m |

Example 20

Removal of Metal Ions from Solution

The samples disclosed in Examples 1-19 were tested to determine their ability to adsorb $Co^{2+}$, $Pb^{2+}$, $Cd^{2+}$ and $Cr^{3+}$ ions from a test solution by determining the distributions ($K_d$) for each of the metals between adsorption on the solid vs. remaining in the solution state. The test solutions were prepared by dissolving cobalt acetate, lead acetate, cadmium acetate and chromium nitrate in tap water. These test solutions were analyzed by ICP and with the first test solution containing 23.5 ppm $Co^{2+}$, 13.5 ppm $Pb^{2+}$, 22.4 ppm $Cd^{2+}$ and 13.6 ppm $Cr^{3+}$, while a second test solution contained 26.7 ppm $Co^{2+}$, 21.6 ppm $Pb^{2+}$, 24.9 ppm $Cd^{2+}$ and 19.2 ppm $Cr^{3+}$. For the test, 200 mg of ion-exchanger is placed in a 30 ml borosilicate vial to which 20 ml of metals-containing test solution is added using a 20 ml syringe. The loaded vial is sealed with a cap and placed in a Bohdan shaker and shaken vigorously for 24 hours at room temperature. Once the ion-exchanger has been contacted with the metals solution for the desired amount of time, the solution/solid suspension is removed from the vial using a syringe. Solids were separated from the solution by pushing the syringe contents through a 0.45 um Nylon filter. The solution was collected in a plastic vial and sent for chemical analysis via ICP or ICP/mass spec. The detection level for $Co^{2+}$, $Cd^{2+}$ and $Cr^{3+}$ was 80 ppb, while the detection level for $Pb^{2+}$ was 0.2 ppm or 200 ppb. It was assumed that the disappearance of the metals from solution were due to adsorption by the solid.

The $K_d$ value for the distribution of metals between solution and solid was calculated using the following formula:

$$K_d \text{ (mL/g)} = \frac{(V)\,(Ac)}{(W)\,(Sc)} 1$$

where: V=volume of waste simulant (mL)
Ac=concentration of cation absorbed on ion-exchanger (g/mL)
W=mass of ion-exchanger evaluated (g)
Sc=concentration of cation in post reaction supernate (g/mL)
Table 18 below summarizes the results of the uptake studies.

TABLE 18

$Co^{2+}$, $Pb^{2+}$, $Cd^{2+}$ and $Cr^{3+}$ distribution expressed as $K_d$ values.

| Example | $Co^{2+}$ $K_d$ (mg/ml) | $Pb^{2+}$ $K_d$ (mg/ml) | $Cd^{2+}$ $K_d$ (mg/ml) | $Cr^{3+}$ $K_d$ (mg/ml) |
|---|---|---|---|---|
| 1 | >29275 | >6650 | >27900 | 15011 |
| 2 | >29275 | >6650 | >27900 | >16900 |
| 3 | 12268 | >6650 | 14833 | >16900 |
| 4 | >29275 | >6650 | >27900 | 3575 |
| 5A | >29275 | >6650 | >27900 | >16900 |
| 5B | >29275 | >6650 | >27900 | >16900 |
| 6 | >29275 | 4400 | 15900 | 5566 |
| 7A | >29275 | >6650 | >27900 | >16900 |
| 7B | >29275 | >6650 | >27900 | >16900 |
| 7C | >29275 | >6650 | >27900 | >16900 |
| 7D | >29275 | >6650 | >27900 | >16900 |
| 8 | 8003 | 6650 | 4877 | >16900 |
| 9 | 16686 | >6650 | >27900 | >16900 |
| 10 | 10169 | >10700 | >31025 | >23900 |
| 11 | >33275 | 3500 | 22536 | 3210 |
| 12 | >29275 | >6650 | >27900 | >16900 |
| 13 | >33275 | >10700 | >31025 | >23900 |
| 14 | 10580 | >10700 | >31025 | >23900 |
| 15 | >33275 | >10700 | >31025 | >23900 |
| 16 | >29275 | >6650 | >27900 | >16900 |
| 17 | >29275 | >6650 | >27900 | >16900 |
| 18A | 3356 | >6650 | 4048 | >16900 |
| 18B | | >6650 | | >16900 |
| 19 | 11508 | >10700 | 16500 | >23900 |

The criterion for including an ion-exchanger in this application is that it had to remove at least 95% of the test metal from solution when evaluated in the test above. A $K_d$=1900 corresponds to 95% removal of the metal cation, so the $K_d$ had to be higher than 1900. The lowest $K_d$ value in this table is $K_d$=3210, corresponding to 97% removal of metal from solution, while the highest value, $K_d$>31025 corresponds to >99.7% removal of metal from solution. All of these ion-exchangers have exhibited excellent performance in removing the respective metals.

Specific Embodiments

While the following is described in conjunction with specific embodiments, it will be understood that this description is intended to illustrate and not limit the scope of the preceding description and the appended claims.

A first embodiment of the invention is a process for removing $Co^{2+}$, $Pb^{2+}$, $Cd^{2+}$, $Cr^{3+}$ toxins or mixtures thereof from bodily fluids comprising contacting the fluid containing the toxins with an ion exchanger to remove the toxins from the fluid by ion exchange between the ion exchanger and the bodily fluid, the ion exchanger selected from zirconium metallate, titanium metallate, tin metallate, multinary metallate containing more than one of zirconium, titanium and tin, and mixtures thereof, the metallates respectively having an empirical formula on an anhydrous basis of:

$$A_m Zr_a Ti_b Sn_c M_d Si_x O_y$$

where A is an exchangeable cation comprising potassium ion, sodium ion, rubidium ion, cesium ion, calcium ion, magnesium ion, hydronium ion or mixtures thereof, M is at least one framework metal selected from the group consisting of hafnium (4+) or niobium (5+), "m" is a mole ratio of A to total metal (total metal=Zr+Ti+Sn+M) and has a value from 0.10 to 15, "a" is a mole fraction of total metal that is Zr and has a value from zero to 1, "b" is a mole fraction of total metal that is Ti and has a value from zero to 1, "c" is a mole fraction of total metal that is Sn and has a value from zero to 1, where a+b+c>0, "d" is a mole fraction of total metal that is M and has a value from zero to less than 1, where a+b+c+d=1 and, "x" is a mole ratio of Si to total metal and has a value from 0 to 12, and "y" is a mole ratio of 0 to total metal and has a value from 2.1 to about 33. An embodiment of the invention is one, any or all of prior embodiments in this paragraph up through the first embodiment in this paragraph wherein the bodily fluid is selected from the group consisting of whole blood, blood plasma, or other component of blood, gastrointestinal fluids and dialysate solution containing blood, blood plasma, other component of blood or gastrointestinal fluids. An embodiment of the invention is one, any or all of prior embodiments in this paragraph up through the first embodiment in this paragraph where M is hafnium (+4) or niobium. An embodiment of the invention is one, any or all of prior embodiments in this paragraph up through the first embodiment in this paragraph where x=0. An embodiment of the invention is one, any or all of prior embodiments in this paragraph up through the first embodiment in this paragraph where a+c+d=0. An embodiment of the invention is one, any or all of prior embodiments in this paragraph up through the first embodiment in this paragraph where A is a mixture of calcium and sodium. An embodiment of the invention is one, any or all of prior embodiments in this paragraph up through the first embodiment in this paragraph wherein the ion exchanger is packed into hollow fibers incorporated into a membrane. An embodiment of the invention is one, any or all of prior embodiments in this paragraph up through the first embodiment in this paragraph wherein the ion exchanger is contained on particles coated with a coating comprising a cellulose derivative composition. An embodiment of the invention is one, any or all of prior embodiments in this paragraph up through the first embodiment in this paragraph wherein the process is a hemoperfusion process wherein the bodily fluid is passed through a column containing the ion exchanger. An embodiment of the invention is one, any or all of prior embodiments in this paragraph up through the first embodiment in this paragraph wherein a dialysate solution is introduced into a peritoneal cavity and then is flowed through at least one adsorbent bed containing at least one of the ion exchanger. An embodiment of the invention is one, any or all of prior embodiments in this paragraph up through the first embodiment in this paragraph wherein the ion exchanger is formed into a shaped article to be ingested orally, followed by ion exchange between the ion exchanger and the $Co^{2+}$, $Pb^{2+}$, $Cd^{2+}$, $Cr^{3+}$ toxins contained in a gastrointestinal fluid in a mammal's intestines and then by excretion of the ion exchanger containing the toxins. An embodiment of the invention is one, any or all of prior embodiments in this paragraph up through the first embodiment in this paragraph wherein the shaped article is coated with a coating that is not dissolved by conditions within a stomach.

A second embodiment of the invention is a composition comprising a combination of a bodily fluid, a dialysate solution or a mixture of the bodily fluid and the dialysate solution the combination further comprising an ion exchanger selected from zirconium metallate, titanium metallate, tin metallate, multinary metallate containing more than one of zirconium, titanium and tin, and mixtures thereof, the metallates respectively having an empirical formula on an anhydrous basis of $$A_m Zr_a Ti_b Sn_c M_d Si_x O_y$$

where A is an exchangeable cation comprising potassium ion, sodium ion, rubidium ion, cesium ion, calcium ion, magnesium ion, hydronium ion or mixtures thereof, M is at least one framework metal selected from the group consisting of hafnium (4+) or niobium (5+), "m" is a mole ratio of A to total metal (total metal=Zr+Ti+Sn+M) and has a value from 0.10 to 15, "a" is a mole fraction of total metal that is Zr and has a value from zero to 1, "b" is a mole fraction of total metal that is Ti and has a value from zero to 1, "c" is a mole fraction of total metal that is Sn and has a value from zero to 1, where a+b+c>0, "d" is a mole fraction of total metal that is M and has a value from zero to less than 1, where a+b+c+d=1 and, "x" is a mole ratio of Si to total metal and has a value from 0 to 12, and "y" is a mole ratio of 0 to total metal and has a value from 2.1 to about 33. An embodiment of the invention is one, any or all of prior embodiments in this paragraph up through the second embodiment in this paragraph wherein the bodily fluid is whole blood, blood plasma, other blood component or gastrointestinal fluid.

A third embodiment of the invention is an apparatus comprising a matrix containing a support material for an ion exchanger selected from zirconium metallate, titanium metallate, tin metallate, multinary metallate containing more than one of zirconium, titanium and tin, and mixtures thereof, the metallates respectively having an empirical formula on an anhydrous basis of $$A_m Zr_a Ti_b Sn_c M_d Si_x O_y$$

where A is an exchangeable cation comprising potassium ion, sodium ion, rubidium ion, cesium ion, calcium ion, magnesium ion, hydronium ion or mixtures thereof, M is at least one framework metal selected from the group consisting of hafnium (4+) or niobium (5+), "m" is a mole ratio of A to total metal (total metal=Zr+Ti+Sn+M) and has a value from 0.10 to 15, "a" is a mole fraction of total metal that is Zr and has a value from zero to 1, "b" is a mole fraction of total metal that is Ti and has a value from zero to 1, "c" is a mole fraction of total metal that is Sn and has a value from zero to 1, where a+b+c>0, "d" is a mole fraction of total metal that is M and has a value from zero to less than 1, where a+b+c+d=1 and, "x" is a mole ratio of Si to total metal and has a value from 0 to 12, and "y" is a mole ratio of 0 to total metal and has a value from 2.1 to about 33. An embodiment of the invention is one, any or all of prior embodiments in this paragraph up through the third embodiment in this paragraph wherein the matrix comprises a porous network comprising biocompatible polymers and metal oxides and silicates. An embodiment of the invention is one, any or all of prior embodiments in this paragraph up through the third embodiment in this paragraph wherein the biocompatible polymers comprise cross-linked carbohydrates or proteins. An embodiment of the invention is one, any or all of prior embodiments in this paragraph up through the third embodiment in this paragraph wherein the biocompatible polymer is a polysaccharide selected from α-glucans having 1,3-, 1,4- or 1,6 linkages. An embodiment of the invention is one, any or all of prior embodiments in this paragraph up through the third embodiment in this paragraph wherein the biocompatible polymer is a carbohydrate selected from glucose, fructose, sucrose, maltose, arabinose, mannose, galactose, lactose and oligomers and polymers comprising one or more of the carbohydrates. An embodiment of the invention is one, any or all of prior embodiments in this paragraph up through the third embodiment in this paragraph wherein the biocompatible polymer comprises a protein selected from albumin, ovalbumin, casein, myosin, actin, globulin, hemoglobin, myoglobin, gelatin and small peptides.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

We claim as our invention:

1. A process for removing $Co^{2+}$, $Pb^{2+}$, $Cd^{2+}$, $Cr^{2+}$ toxins or mixtures thereof from bodily fluids comprising contacting said bodily fluid containing the toxins with an ion exchanger to remove the toxins from the fluid by ion exchange between said ion exchanger and said bodily fluid, the ion exchanger selected from zirconium metallate, titanium metallate, tin metallate, multinary metallate containing more than one of zirconium, titanium and tin, and mixtures thereof, the metallates respectively having an empirical formula on an anhydrous basis of:

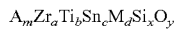

$$A_m Zr_a Ti_b Sn_c M_d Si_x O_y$$

where A is an exchangeable cation comprising potassium ion, sodium ion, rubidium ion, cesium ion, calcium ion, magnesium ion, hydronium ion or mixtures thereof, M is at least one framework metal selected from the group consisting of hafnium (4+) or niobium (5+), "m" is a mole ratio of A to total metal (total metal=Zr+Ti+Sn+M) and has a value from 0.10 to 15, "a" is a mole fraction of total metal that is Zr and has a value from zero to 1, "b" is a mole fraction of total metal that is Ti and has a value from zero to 1, "c" is a mole fraction of total metal that is Sn and has a value from zero to 1, where a+b+c >0, "d" is a mole fraction of total metal that is M and has a value from zero to less than 1, where a+b+c+d=1 and, "x" is a mole ratio of Si to total metal and has a value from 0 to 12, and "y" is a mole ratio of O to total metal and has a value from 2.1 to 33.

2. The process of claim 1 wherein the bodily fluid is selected from the group consisting of whole blood, blood plasma, or other component of blood, gastrointestinal fluids and dialysate solution containing blood, blood plasma, other component of blood or gastrointestinal fluids.

3. The process of claim 1 where M is hafnium (+4) or niobium.

4. The process of claim 1 where x=0.

5. The process of claim 1 where a +c+d=0.

6. The process of claim 1 where A is a mixture of calcium and sodium.

7. The process of claim 1 wherein the ion exchanger is packed into hollow fibers incorporated into a membrane.

8. The process of claim 1 wherein said ion exchanger is contained on particles coated with a coating comprising a cellulose derivative composition.

9. The process of claim 1 wherein said process is a hemoperfusion process wherein said bodily fluid is passed through a column containing said ion exchanger.

10. The process of claim 1 wherein a dialysate solution is introduced into a peritoneal cavity and then is flowed through at least one adsorbent bed containing at least one of said ion exchanger.

11. The process of claim 1 wherein said ion exchanger is formed into a shaped article to be ingested orally, followed by ion exchange between said ion exchanger and said $Co^{2+}$, $Pb^{2+}$, $Cd^{2+}$, $Cr^{2+}$ toxins contained in a gastrointestinal fluid in a mammal's intestines and then by excretion of said ion exchanger containing said toxins.

12. The process of claim 11 wherein said shaped article is coated with a coating that is not dissolved by conditions within a stomach.

* * * * *

UNITED STATES PATENT AND TRADEMARK OFFICE
CERTIFICATE OF CORRECTION

PATENT NO. : 11,964,266 B2
APPLICATION NO. : 16/506377
DATED : April 23, 2024
INVENTOR(S) : Gregory John Lewis et al.

It is certified that error appears in the above-identified patent and that said Letters Patent is hereby corrected as shown below:

In the Claims

Claim 1, in Column 29, Line 8 should read as follows:
1. A process for removing $Co^{2+}$, $Pb^{2+}$, $Cd^{2+}$, $Cr^{3+}$ toxins Claim 11, in Column 30, Line 27 should read as follows:
$Pb^{2+}$, $Cd^{2+}$, $Cr^{3+}$ toxins contained in a gastrointestinal fluid Signed and Sealed this
Thirtieth Day of July, 2024

Katherine Kelly Vidal
*Director of the United States Patent and Trademark Office*